US012257419B2

(12) United States Patent
Nunez et al.

(10) Patent No.: US 12,257,419 B2
(45) Date of Patent: *Mar. 25, 2025

(54) MEDICAL DEVICE WITH AUTOMATED MODALITY SWITCHING

(71) Applicant: CareFusion 303, Inc., San Diego, CA (US)

(72) Inventors: Carlos M. Nunez, Carlsbad, CA (US); James Alwan, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 398 days.

This patent is subject to a terminal disclaimer.

(21) Appl. No.: 17/721,663

(22) Filed: Apr. 15, 2022

(65) Prior Publication Data

US 2022/0347385 A1 Nov. 3, 2022

Related U.S. Application Data

(63) Continuation of application No. 14/738,601, filed on Jun. 12, 2015, now Pat. No. 11,324,886.

(51) Int. Cl.
| | |
|---|---|
| *A61M 5/172* | (2006.01) |
| *G16H 20/17* | (2018.01) |
| *G16H 40/67* | (2018.01) |
| *A61M 5/14* | (2006.01) |
| *A61M 16/00* | (2006.01) |

(52) U.S. Cl.
CPC ............ *A61M 5/172* (2013.01); *G16H 20/17* (2018.01); *G16H 40/67* (2018.01); *A61M 5/14* (2013.01); *A61M 5/1723* (2013.01); *A61M 16/0003* (2014.02); *A61M 2205/14* (2013.01); *A61M 2205/3306* (2013.01); *A61M 2205/3561* (2013.01); *A61M 2205/502* (2013.01); *A61M 2205/505* (2013.01); *A61M 2205/52* (2013.01); *A61M 2205/6072* (2013.01)

(58) Field of Classification Search
CPC .............. A61M 2205/14; A61M 5/172; A61M 5/1723; A61M 5/14; G16H 40/67; G16H 20/17

See application file for complete search history.

(56) References Cited

U.S. PATENT DOCUMENTS

| | | | |
|---|---|---|---|
| 5,651,775 A | * | 7/1997 | Walker .............. A61M 5/31533 604/207 |
| 5,873,731 A | | 2/1999 | Prendergast |
| 6,593,528 B2 | | 7/2003 | Franklin-Lees et al. |
| 8,255,585 B2 | | 8/2012 | Levin |

(Continued)

*Primary Examiner* — Jenna Zhang

(74) *Attorney, Agent, or Firm* — Mintz Levin Cohn Ferris Glovsky and Popeo, P.C.

(57) ABSTRACT

A medical device such as an infusion system detects that an accessory has been coupled to the device. The medical device initially operates in a first mode of operation. The medical device, in response to the detecting, associates the accessory with a different mode of operation for the medical device that requires changes to at least one of the operating parameters for the infusion system or elements within a graphical user interface. The medical device then automatically changes the mode of operation from the first mode of operation to the associated different mode of operation to reflect the coupling of the accessory to the infusion system. Related apparatus, systems, techniques and articles are also described.

16 Claims, 3 Drawing Sheets

(56) References Cited

U.S. PATENT DOCUMENTS

| | | | |
|---|---|---|---|
| 8,312,877 B2 | 11/2012 | Elaz et al. | |
| 9,800,663 B2 | 10/2017 | Arrizza | |
| 11,324,886 B2* | 5/2022 | Nunez | G16H 20/17 |
| 2001/0056258 A1* | 12/2001 | Evans | G16H 20/17 |
| | | | 128/DIG. 13 |
| 2004/0092885 A1* | 5/2004 | Duchon | A61M 5/14546 |
| | | | 700/282 |
| 2004/0172302 A1 | 9/2004 | Martucci et al. | |
| 2005/0107923 A1* | 5/2005 | Vanderveen | G16H 20/17 |
| | | | 700/282 |
| 2005/0277890 A1 | 12/2005 | Stewart et al. | |
| 2006/0224128 A1 | 10/2006 | Lurvey et al. | |
| 2007/0088249 A1 | 4/2007 | Duffy et al. | |
| 2007/0156092 A1 | 7/2007 | Estes et al. | |
| 2009/0143916 A1 | 6/2009 | Boll et al. | |
| 2011/0197883 A1 | 8/2011 | McDaniel et al. | |
| 2012/0030611 A1 | 2/2012 | Skidmore | |
| 2013/0090602 A1* | 4/2013 | Avery | A61M 5/24 |
| | | | 604/189 |
| 2013/0123743 A1* | 5/2013 | Adams | A61M 5/16831 |
| | | | 604/151 |
| 2013/0150824 A1* | 6/2013 | Estes | A61M 5/14244 |
| | | | 604/151 |
| 2013/0197471 A1* | 8/2013 | Williams | A61M 5/365 |
| | | | 604/247 |
| 2014/0276575 A1* | 9/2014 | Vanderveen | A61M 1/3644 |
| | | | 604/67 |
| 2014/0378898 A1* | 12/2014 | Rosinko | A61M 5/5086 |
| | | | 604/111 |
| 2015/0205923 A1 | 7/2015 | Sobie | |
| 2017/0017786 A1 | 1/2017 | Siebert et al. | |

\* cited by examiner

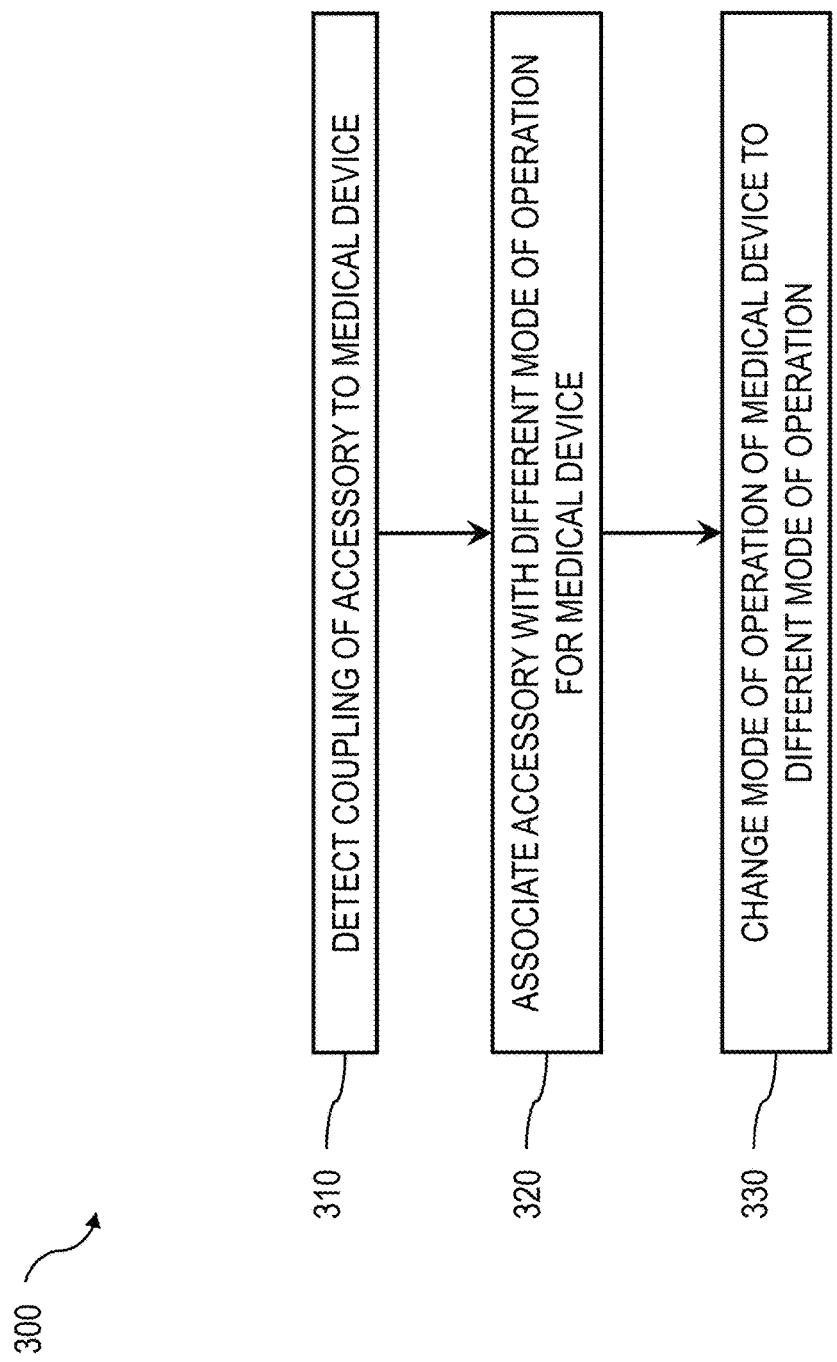

MEDICAL DEVICE WITH AUTOMATED MODALITY SWITCHING

CROSS REFERENCE TO RELATED APPLICATIONS

This application is a continuation of U.S. patent application Ser. No. 14/738,601 filed on Jun. 12, 2015. The full disclosure is incorporated herein by reference in its entirety.

TECHNICAL FIELD

The subject matter described herein relates to a medical device in which its mode of operation automatically switches in response to the coupling of one or more accessories

BACKGROUND

Medical devices such as infusion systems and ventilators are complex and must operate under a variety of clinical conditions. Such medical devices may deliver multiple functionalities depending on the circumstance including the patient, caregiver, and location. However, such functionalities are often dependent on the care to be administered by the device. Most medical devices are not well equipped to respond to environmental cues and adapt to meet imminent needs of the care for the patient.

SUMMARY

In one aspect, an infusion system detects that an accessory has been coupled to the infusion system. The infusion system is configured to administer medication to a patient and includes at least one data processor, memory, and a display for rendering a graphical user interface. Further, the infusion system initially operates in a first mode of operation. The infusion system, in response to the detecting, associates the accessory with a different mode of operation for the infusion system that requires changes to at least one of the operating parameters for the infusion system or elements within the graphical user interface. The infusion system then automatically changes the mode of operation from the first mode of operation to the associated different mode of operation to reflect the coupling of the accessory to the infusion system.

The accessory can take many different forms. Example accessories include a patient controlled analgesia (PCA) pump, a syringe pump, an enteral pump, an elastomeric pump, a peristaltic pump, a multi-channel pump, and a large volume pump.

The accessory can also be a tubing set through which the medication flows to the patient.

The accessory can be a vital signs monitoring sensor.

The detecting can include detecting that the accessory is physically connected to the infusion system. The detecting can include initiating wireless communication between the accessory and the infusion system.

The detecting can also or additionally include various optical, electrical, electromechanical, magnetic and other switching/detection methodologies. For example, the coupling of the accessory to the infusion system can be detected by an optical sensor integrated into the infusion system. In such cases, the optical sensor can detect an indicator such as a bar code or optical pattern on the accessory. In addition, the coupling of the accessory to the infusion system can be detected by a switch that is triggered upon mechanically coupling the accessory to the infusion system. Further, the coupling of the accessory to the infusion system can detected via electromagnetic fields or electromagnetic induction.

The associating can include polling a remote computing device to receive data to associate the detected accessory with the different mode of operation. Data can be received from the remote computing device that specifies parameters or restrictions regarding the administration of medication to the patient such that the different mode of operation takes into account such specified parameters or restrictions. The parameters regarding administration of medication to the patient can include a prescription for the patient. The restrictions regarding administration of medication to the patient can be associated with allergies of the patient.

The changing can, in some cases, include polling a remote computing device to obtain a software or firmware update for the infusion system.

In another variation, a ventilator can detect that an accessory has been coupled to the ventilator. The ventilator is configured to assist a patient with his or her breathing function and includes at least one data processor, memory, and a display for rendering a graphical user interface. The ventilator initially operates in a first mode of operation. Thereafter, the ventilator, in response to the detecting, associates the accessory with a different mode of operation for the ventilator. The different mode of operation requires changes to at least one of: operating parameters for the ventilator and elements within the graphical user interface. Thereafter, the ventilator automatically changes the mode of operation from the first mode of operation to the associated different mode of operation to reflect the coupling of the accessory to the ventilator.

In still a further interrelated aspect, a medical device detects that an accessory has been coupled to the medical device. The medical device includes least one data processor, memory, and at least one mechanically actuatable element. In addition, the medical device initially operates in a first mode of operation. The medical device, in response to the detecting, associates the accessory with a different mode of operation for the medical device. The different mode of operation requires changes to at least one operating parameter associated with the at least one mechanically actuatable element. Subsequently, the medical device automatically changes the mode of operation from the first mode of operation to the associated different mode of operation to reflect the coupling of the accessory to the medical device.

In yet a further interrelated aspect, a medical device system detects that an accessory has been coupled to the device. The medical device initially operates in a first mode of operation. The medical device, in response to the detecting, associates the accessory with a different mode of operation for the medical device that requires changes to at least one of the operating parameters for the infusion system or elements within a graphical user interface. The medical device then automatically changes the mode of operation from the first mode of operation to the associated different mode of operation to reflect the coupling of the accessory to the infusion system.

Non-transitory computer program products (i.e., physically embodied computer program products) are also described that store instructions, which when executed by one or more data processors of one or more computing systems, causes at least one data processor to perform operations herein. Similarly, computer systems are also described that may include one or more data processors and memory coupled to the one or more data processors. The memory may temporarily or permanently store instructions that cause at least one processor to perform one or more of the operations described herein. In addition, methods can be implemented by one or more data processors either within a single computing system or distributed among two or more computing systems. Such computing systems can be connected and can exchange data and/or commands or other instructions or the like via one or more connections, including but not limited to a connection over a network (e.g. the Internet, a wireless wide area network, a local area network, a wide area network, a wired network, or the like), via a direct connection between one or more of the multiple computing systems, etc.

The subject matter described herein provides many technical advantages. For example, the current subject matter provides enhanced usability for medical devices such as infusion systems and ventilators by automatically changing a mode of operation when an accessory is coupled to such medical devices.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

FIG. 3 is a process flow diagram illustrating automated switching of operating modalities of a medical device.

Like reference symbols in the various drawings indicate like elements.

DETAILED DESCRIPTION

Figure 1:
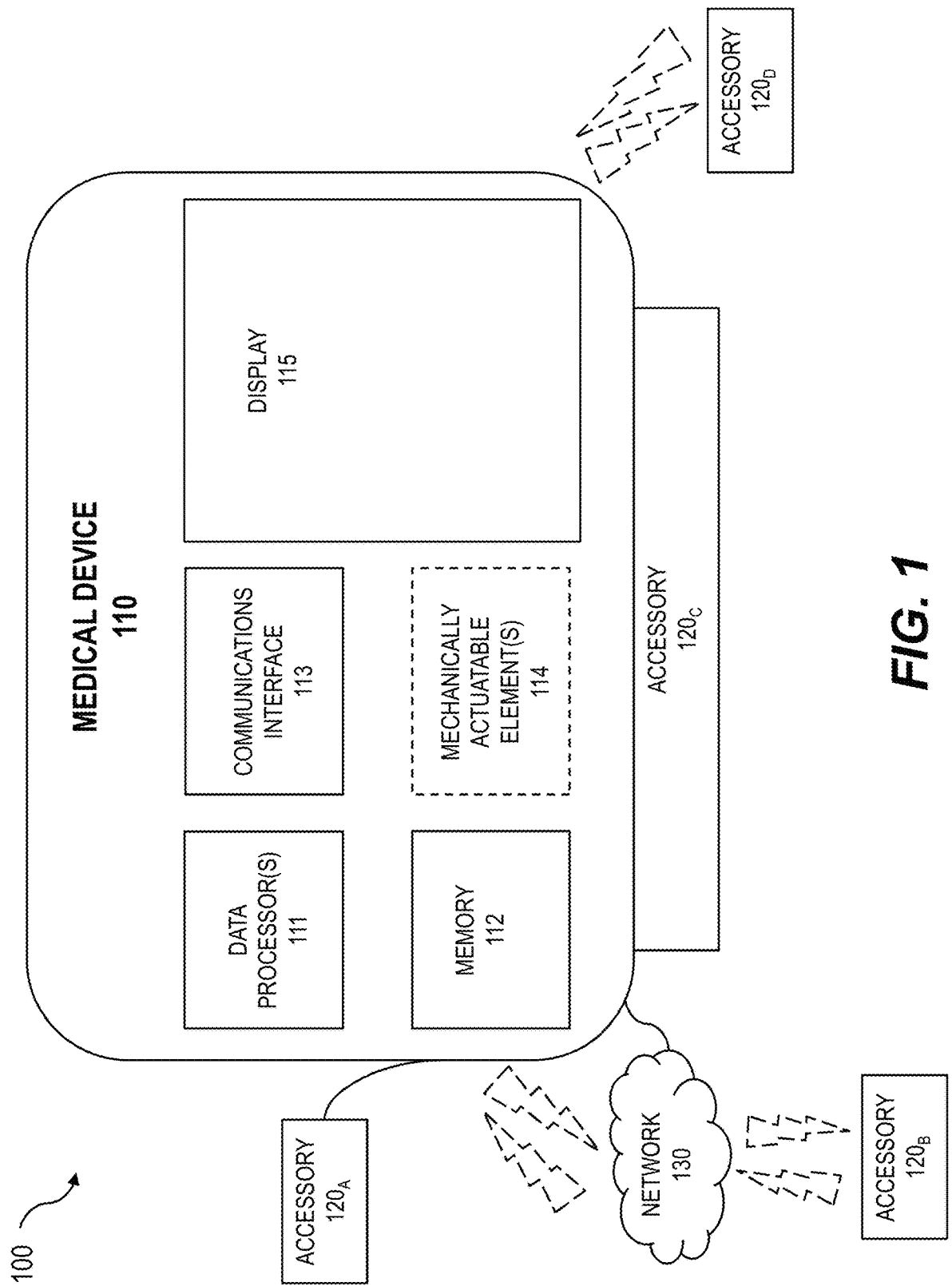
FIG. 1 is a logic diagram illustrating a medical device.

FIG. 1 is a block diagram 100 illustrating a medical device 110 used in connection with the treatment of a patient. Example medical devices 110 include, but are not limited to, infusion systems (i.e., systems configured to administer fluid such as medication and food to a patient, etc.) and ventilators (i.e., systems configured to assist a patient with his or her breathing function). The medical device 100 can include at least one hardware data processor 111 (which can be a multi-core processor) and memory 112 storing instructions for execution by the at least one data processor. In addition, the medical device 110 can include a communications interface 113 which, depending on the desired implementation, can communicate with external devices/computer networks that are physically connected to the medical device 110 and/or which are in direct or indirect communication with the medical device 110 via a wired and/or wireless communications network.

The medical device 110 can additionally and optionally include at least one mechanically actuatable element 114 that can have variable operating modes (e.g., variable speeds, active/non-active, etc.). Examples of mechanically actuatable elements 114 include, for example, a pump used for infusion of fluids to a patient and a pump to deliver gas to a patient for breathing purposes.

The medical device 110 can also include a display 115 that renders a graphical user interface that characterizes various aspects regarding the operation of the medical device 110. In some implementations, the graphical user interface displayed in the display 115 includes a plurality of graphical user interface elements which, when activated via user-generated input, causes either a mode of operation of the medical device 110 to change and/or a view presented in the graphical user interface of the display 115 to change. The user-generated input can be via various modalities including, for example, the display 115 if it includes a capacitive or other touch screen interface, mechanical buttons/knobs/sliders external to the display 115, and the like.

The medical device 110 can be coupled to one or more accessories 120 that form part of the functionality offered by the medical device 110 (e.g., change the manner in which the at least one mechanically actuatable elements 114 operate, etc.) and/or which cause the graphical user interface (GUI) rendered within the display 115 to change (e.g., a different view can be displayed in the GUI, etc.). The accessories 120 can take a wide variety of forms including components required for the operation of the medical device 110, sensors for use by the medical device 110, and/or other medical devices involved with the treatment/care of a patient.

The accessories 120 can be coupled to the medical device 110 in a variety of manners. For example, the accessory $120_A$ can be connected by a wire/socket providing either unidirectional communication from the accessory $120_A$ to the medical device 110 or providing bi-directional communication. For example, the accessory $120_A$ can be a vital signs monitor such as a pulse oximeter, a set of electrocardiogram electrodes (collectively ECG), heart rate monitor, blood pressure monitor, as well as other types of physiological/vital sign monitors. In some cases, such as with pulse oximeters, signals are transmitted from the accessory $120_A$ to the medical device 110 and not vice versa. With other cases, the accessory $120_A$ can receive signals from the medical device 110 such as the activation of a blood pressure cuff.

Similar to the hard-wired accessory $120_A$, other accessories $120_B$ and $120_D$ can be coupled to the medical device 110 either directly via peer-to-peer unidirectional or bi-directional communication (as with accessory $120_D$) or indirectly via unidirectional or bi-directional communication over a network 130 (as with accessory $120_B$) which may be wired and/or wireless. These accessories $120_E$ and $120_D$, while not directly connected to the medical device 110 can have similar functionality to the accessory $120_A$ which is hard-wired to the medical device 110 (as described above). The network 130 can be, for example, a local area Intranet, a hospital information system, the Internet, and the like.

In other cases, the accessory $120_C$ can be physically connected to the medical device 110 either directly or via an adapter or other mechanism. For example, in the case of the medical device 110, the accessory $120_C$ can be an infusion module such as a syringe pump module, a patient controlled analgesia (PCA) module, an enteral pump, an elastomeric pump, a peristaltic pump, a multi-channel pump, or a large volume pump. The accessory 120c can also be a disposable element for use by the medical device 110 such as a tubing set or other adapter. For example, different tubing sets can, for example, implicate different caregiving modalities. Opaque tubing sets can be used in some applications and/or some tubing sets can act as chemical barriers. Tubing sets can be coded, for example, by an RFID chip, a bar code, a QR code, an optical code, or other, and identified by the medical device 110 and the medical device 110 can automatically switch to the appropriate configuration for providing care to the patient. For example, a tubing set that is coded for use with a neonate, would automatically switch the controls, alarms, settings, and other functions appropriate for a neonate rather than an adult.

The accessory 120, need not be a tubing set but, rather, can take the form of disposables. For example, the accessory can be a disposable element used for chemotherapy, a syringe for manual administration of medication, epidural disposable, enteral disposable, per-enteral disposable as well as other types of equipment used to deliver fluid to a patient (in the case the case of infusion systems) or gas to a patient (in the case of ventilators).

The medical device 110 can detect the coupling of an accessory 120 to it. Coupling, in this regard (unless otherwise specifically specified), can include one or more of: the wired connection of an accessory $120_A$ to the medical device 110, the initiation of communication by the medical device 110 with an accessory $120_B$ via a network, a direct mechanical/physical coupling of an accessory 120c to the medical device 110, or peer-to-peer communication between the medical device 110 and an accessory $120_D$. Upon this detection of the coupling of an accessory 120, the medical device 110 can, in some cases, change a mode of operation of the medical device 110. This changing can be based, for example, by accessing a local or remote (via the network 130) rules engine/lookup table/server to determine whether or not any changes to the mode of operation medical device 110 should occur in response to the detection of the accessory 120 coupling.

The detection of the coupling can occur when the communications interface 113 initiates communication by receiving data/signals from an accessory $120_B$, D or by initiating bi-directional communication with an accessory $120_{B, D}$. With the latter, there may be initial handshaking/discovery which is used to initiate the communication and the detection can be considered to occur once such discovery has been completed. Similar handshaking/discovering can occur in connection with a wired accessory $120_A$ as part of establishing unidirectional or bidirectional communication (via the communications interface 113).

In some variations, the detection of the coupling of an accessory 120 can cause an alarm to be triggered and/or to cause the medical device 110 to cease operation. Such an arrangement is advantageous to avoid misconnections or reconnections in which an accessory 120 is inadvertently connected to the wrong medical device 110 (either because of compatibility issues or particular patient care). For example, the current subject matter can be used to detect the misconnection of an air cuff to an IV line. The alarms can be visual indicators (changes in colors to the GUI), audio indicators, and/or vibratory indicators.

In other variations, the detection of the coupling can occur when the accessory $120_C$ is being physically connected to the medical device 110 or in physical proximity thereof. The physical connection can be detected, for example, using a switch which is mechanically tripped when the accessory $120_C$ is mechanically connected to the medical device 110. In the addition or in the alternative, proximity sensors can form part of the medical device 110 that can be used to detect when the accessory $120_C$ is coupled to the medical device 110. Other type of proximity technologies can be used including integrated bar code scanners and other optical technologies, magnetic elements/switches, electromechanical element/switches and the like. In some variations, the medical device 110 can include a proximity sensor that detect a corresponding signal from the accessory via electromagnetic fields/electromagnetic induction such as, Radio-Frequency Identification (RFID), Near Field Communication (NFC), and the like. In other variations, the medical device 110 can include an optical sensor that includes an optical sensor to scan or otherwise capture a visual identifier (e.g., bar code, optical pattern, etc.) on the accessory $120_C$ (or in some cases on an identifier worn by the patient).

After the detection, the medical device 110 can associate the coupled accessory 120 with a different mode of operation and cause the medical device 110 to commence operation according to such different mode operation. The different mode of operation can include automatically changing one or more operating parameters of the medical device 110 and/or changing elements within the GUI rendered in the display 115 (i.e., a different GUI view can be displayed). This changing can, for example, be automatic in that it is implemented by the medical device 110 without any clinician intervention. In some variations, the GUI rendered in the display 115 can provide a prompt to a caregiver to approve the change of the mode of operation of the medical device 110 (upon the detection of coupling of the accessory 120).

In some cases, changing the mode of operation can include changing one or more operating parameters associated with the mechanically actuatable element(s) 114. For example, the mechanically actuatable element 114 can be a pump that is used by the accessory 120 for various purposes such as fluid infusion or gas delivery to a patient. The changes in mode of operation can accommodate different flow rates, operating time periods, periodicity of operation, and the like.

In other variations, changing of the mode of operation can include updating software/firmware that is executed by the medical device 110. In such implementations, the medical device 110, in response to the detection of the coupling of the accessory 120, can poll a remote computing system/device to indicate such coupling, and such remote computing system/device can reply with data encapsulating information required for such an update of the software/firmware. For example, a software update can include a new/expanded drug library associated with the accessory 120. This drug library can be obtained, for example, by polling a hospital pharmacy system with an identification associated with the medical device 110 and/or the patient to ensure that the proper drugs/medication/treatment is administered to the patient. The software update can additionally/alternatively include data including a prescription for the patient obtained, for example, from the hospital pharmacy system. The remote computing system/device can also provide information about permitted medications to be administered to the patient as well as related concentrations, doses, and the like. Relatedly, information about allergies and/or medications which cannot be mixed with prescribed medications can be provided. In addition or in the alternative, the polling of the remote computing system can be implemented to ensure, for example, that the medical device 110 is licensed to implement the corresponding operations/actions.

Figure 2:
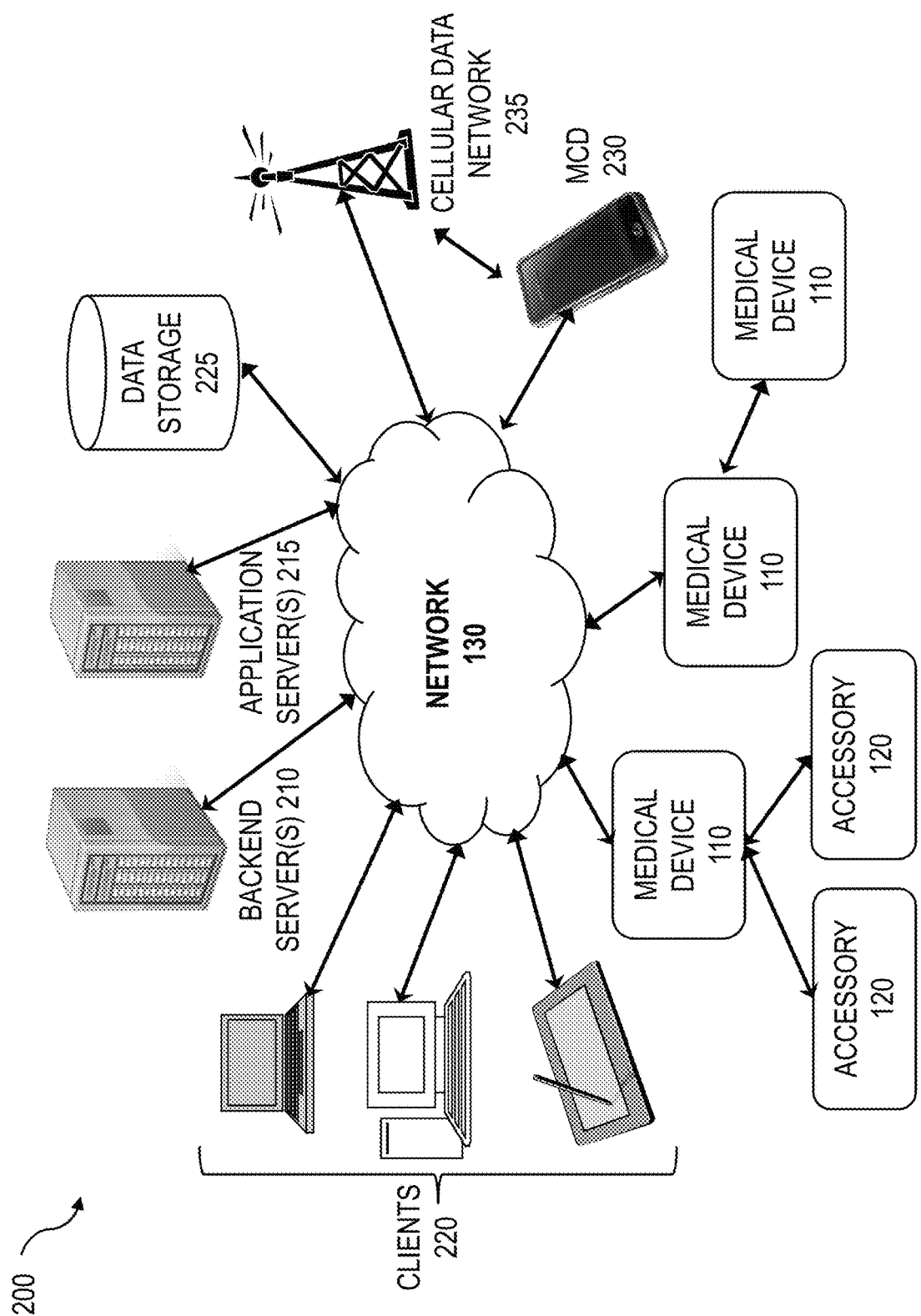
FIG. 2 is a diagram illustrating a healthcare computing environment.

FIG. 2 is a system diagram illustrating a computing landscape 200 within a healthcare environment such as a hospital that includes one or medical devices 110 as described above. Various devices and systems, both local to the healthcare environment and remote from the healthcare environment, can interact via the network 130 (which can be one of a plurality of networks). The computing network 130 can provide any form or medium of digital communication connectivity (i.e., wired or wireless) amongst the various devices and systems. Examples of communication networks include a local area network ("LAN"), a wide area network ("WAN"), and the Internet. In some cases, one or more of the various devices and systems can interact directly via peer-to-peer coupling (either via a hardwired connection or via a wireless protocol such as BLUETOOTH, ZIGBEE, short range radio, WiFi, etc.). In addition, in some variations, one or more of the devices and systems communicate via a cellular data network.

The medical devices 110 can each include at least one communications interface 113 that can access the computing network 130 either via a fixed wired connection or via a wireless connection (via, for example, one or more access points). In addition, the medical devices 110 can also couple to other components within the computing landscape 200 via direct wired or wireless peer-to-peer coupling (not shown). Furthermore, in some cases, the medical devices 110 can be self-contained and are not connected to any other devices or networks. The medical devices 110 can transmit data via the computing network 130 to any of the other components within the landscape 200 that can, for example, characterize the medical device 110. In addition, the medical devices 110 can receive data from the computing network 130 relating to monitoring and in some cases controlling one or more attributes of the medical devices 110 (e.g., software updates, configuration updates, historical data, status information, assets location, patient information, etc.).

In particular, aspects of the computing landscape 200 can be implemented in a computing system that includes a back-end component (e.g., as a data server 210), or that includes a middleware component (e.g., an application server 215), or that includes a front-end component (e.g., a client computer 220 having a graphical user interface or a Web browser through which a user may interact with an implementation of the subject matter described herein), or any combination of such back-end, middleware, or front-end components. A client 220 and server 210, 215 are generally remote from each other and typically interact through the communications network 130. The relationship of the clients 220 and servers 210, 215 arises by virtue of computer programs running on the respective computers and having a client-server relationship to each other. Clients 220 can be any of a variety of computing platforms that include local applications for providing various functionality within the healthcare environment. Example clients 220 include, but are not limited to, desktop computers, laptop computers, tablets, and other computers with touch-screen interfaces. The local applications can be self-contained in that they do not require network connectivity and/or they can interact with one or more of the servers 210, 215 (e.g., a web browser).

A variety of applications can be executed on the various devices and systems within the computing landscape including the medical devices 110 such as electronic health record applications, medical device monitoring, operation, and maintenance applications, scheduling applications, billing applications and the like. As another example, the applications can comprise a collection of enterprise-based applications that provide dose error reduction software (DERS) for the medical devices 110 incorporates a role-based view of infusion data, provides a comprehensive platform for connectivity to external hospital applications, and enables directed maintenance and calibration activities for devices, storage of clinical and device history, etc. As a further example, the applications can provide for remote alarms management and/or asset tracking for the medical devices 110.

The network 130 can be coupled to one or more data storage systems 225. The data storage systems 225 can include databases providing physical data storage within the healthcare environment or within a dedicated facility. In addition, or in the alternative, the data storage systems 225 can include cloud-based systems providing remote storage of data in, for example, a multi-tenant computing environment. The data storage systems 225 can also comprise non-transitory computer readable media.

Mobile communications devices (MCDs) 230 can also form part of the computing landscape 200. The MCDs 230 can communicate directly via the network 130 and/or they can communicate with the network 130 via an intermediate network such as a cellular data network. Various types of communication protocols can be used by the MCDs 230 including, for example, messaging protocols such as SMS and MIMS. In some cases, the MCDs 230 can receive alerts generated from the operation of the medical devices 110 and/or they can otherwise be used to monitor the operation of such medical devices 110.

Various types of medical devices 110 can be used as part of the computing landscape 200. These medical devices 110 can comprise, unless otherwise specified, any type of device or system with a communications interface that characterizes one or more physiological measurements of a patient and/or that characterize or are used for the treatment of a patient. In some cases, the accessories 120 communicate via peer to peer wired or wireless communications with a medical device 110 (as opposed to communicating with the network 130). For example, the accessory 120 can comprise a bedside vital signs monitor that is connected to a medical device 110. One or more attributes of the medical devices 110 can be locally controlled by a clinician, controlled via a clinician via the network 130, and/or they can be controlled by one or more of a server 210, 215, a client 220, or a MCD 230.

The computing landscape 200 can provide various types of functionality as may be required within a healthcare environment such as a hospital. For example, a pharmacy can initiate a prescription via one of the client computers 220. This prescription can be stored in the data storage 225 and/or pushed out to other clients 220, an MCD 230, and/or one or more of the medical devices 110. In addition, the medical devices 110 can provide data characterizing one or more physiological measurements of a patient and/or treatment of a patient (e.g., medical device 110 can be an infusion management system, etc.). The data generated by the medical devices 110 can be communicated to other medical devices 110, the servers 210, 215, the clients 220, the MCDs 230, and/or stored in the data storage systems 225.

Various methods can be implemented in accordance with the current subject matter. FIG. 3 is a process flow diagram 300 in which, at 310, a medical device, such as an infusion system or a ventilator, detects that an accessory has been coupled to it. The medical device includes at least one data processor, memory, and a display for rendering a graphical user interface and initially operates in a first mode of operation. Thereafter, at 320, the medical device associates, in response to the detecting, the accessory with a different mode of operation for the infusion system. The different mode of operation can changes at least one of: operating parameters for the infusion system or elements within the graphical user interface. Subsequently, at 330, the mode of operation of the medical device is automatically changed from the first mode of operation to the associated different mode of operation to reflect the coupling of the accessory to the medical device.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

One or more aspects or features of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device (e.g., mouse, touch screen, etc.), and at least one output device.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid state memory or a magnetic hard drive or any equivalent storage medium. The machine-readable medium can alternatively or additionally store such machine instructions in a transient manner, such as for example as would a processor cache or other random access memory associated with one or more physical processor cores.

With certain aspects, to provide for interaction with a user, the subject matter described herein can be implemented on a computer having a display device, such as for example a cathode ray tube (CRT) or a liquid crystal display (LCD) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

The computing system may include clients and servers. A client and server are generally remote from each other and typically interact through a communication network. The relationship of client and server arises by virtue of computer programs running on the respective computers and having a client-server relationship to each other.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flow(s) depicted in the accompanying figures and/or described herein do not necessarily require the particular order shown, or sequential order, to achieve desirable results. Other implementations may be within the scope of the following claims.

What is claimed is:

1. An infusion system comprising:
   at least one data processor;
   a display adapted to render a graphical user interface; and
   at least one memory including computer program code, the at least one memory and the computer program code configured to, with the at least one data processor, cause the infusion system to:
   detect that a tubing set is being physically connected to the infusion system or is in physical proximity the infusion system, the infusion system being configured to administer medication to a patient via the tubing set;
   communicate with a remote computing system upon detecting that the tubing set is being physically connected to the infusion system or is in physical proximity to the infusion system;
   receive from the remote computing system restrictions related to the infusion system;
   after detecting that the tubing set is physically connected to the infusion system or is in physical proximity to the infusion system:
   cause an alarm to be triggered; and
   receive a firmware update.

2. The infusion system of claim 1, wherein the at least one memory and the computer program code are further configured to, with the at least one data processor, cause the infusion system to cease operation in response to detecting that the tubing set is being physically connected to the infusion system or is in physical proximity to the infusion system.

3. The infusion system of claim 1, wherein the firmware update includes medication data associated with the tubing set.

4. The infusion system of claim 1, wherein the infusion system detects that the tubing set is in physical proximity the infusion system upon the infusion system wirelessly interacting with at least a portion of the tubing set.

5. The infusion system of claim 1, wherein the at least one memory and the computer program code are further configured to, with the at least one data processor, cause the infusion system to modify the graphical user interface on the display.

6. The infusion system of claim 5, wherein a view presented on the graphical user interface on the display is modified.

7. The infusion system of claim 1, wherein the firmware update includes a drug library.

8. The infusion system of claim 1, wherein triggering the alarm includes changing a visual indicator shown on the graphical user interface.

9. A method of operating an infusion system, comprising:
  detecting, by the infusion system, that a tubing set is being physically connected to the infusion system or is in physical proximity the infusion system, the infusion system being configured to administer medication to a patient via the tubing set;
  communicating with, by the infusion system, a remote computing system upon detecting that the tubing set is being physically connected to the infusion system or is in physical proximity to the infusion system;
  receiving, by the infusion system, from the remote computing system restrictions related to the infusion system; and
  after detecting that the tubing set is physically connected to the infusion system or is in physical proximity to the infusion system:
    causing, by the infusion system, an alarm to be triggered; and
    receiving, by the infusion system, a firmware update.

10. The method of claim 9, further comprising causing the infusion system to cease operation in response to detecting that the tubing set is being physically connected to the infusion system or is in physical proximity to the infusion system.

11. The method of claim 9, wherein the firmware update includes medication data associated with the tubing set.

12. The method of claim 9, wherein the infusion system detects that the tubing set is in physical proximity to the infusion system upon the infusion system wirelessly interacting with at least a portion of the tubing set.

13. The method of claim 9, further comprising causing the infusion system to modify a graphical user interface on a display.

14. The method of claim 13, wherein a view presented on the graphical user interface on the display is modified.

15. The method of claim 9, wherein the firmware update includes a drug library.

16. The method of claim 9, wherein causing the alarm to be triggered includes changing a visual indicator shown on a graphical user interface associated with the infusion system.

* * * * *